US009986941B2

(12) United States Patent
Lee et al.

(10) Patent No.: US 9,986,941 B2
(45) Date of Patent: Jun. 5, 2018

(54) METHODS AND APPARATUS FOR RAPID MONITORING OF HEMOSTATIC STATE (71) Applicant: The Board of Trustees of the Leland Stanford Junior University, Palo Alto, CA (US)

(72) Inventors: Meredith M. Lee, El Cerrito, CA (US); Jelena Levi, San Francisco, CA (US); James L. Zehnder, Menlo Park, CA (US); James S. Harris, Jr., Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days. days.

(21) Appl. No.: 14/752,144

(22) Filed: Jun. 26, 2015

(65) Prior Publication Data
US 2015/0374269 A1 Dec. 31, 2015

Related U.S. Application Data (60) Provisional application No. 62/017,571, filed on Jun. 26, 2014.

(51) Int. Cl.
| *A61B 5/145* | (2006.01) |
| *G01N 21/64* | (2006.01) |
| *A61B 5/1455* | (2006.01) |
| *C12Q 1/56* | (2006.01) |
| *A61B 5/00* | (2006.01) |

(52) U.S. Cl.
CPC ...... *A61B 5/14556* (2013.01); *A61B 5/14546* (2013.01); *C12Q 1/56* (2013.01); *G01N 21/6428* (2013.01); *A61B 5/14557* (2013.01); *G01N 2021/6432* (2013.01)

(58) Field of Classification Search
CPC ..... B01L 2400/0406; B01L 2400/0403; B01L 2400/04; B01L 2400/00; A61B 5/145; A61B 5/00
USPC .......................................... 422/50
See application file for complete search history.

(56) References Cited

U.S. PATENT DOCUMENTS

| 8,277,384 B2 | 10/2012 | Fine |
| 8,293,493 B2 | 10/2012 | Coll et al. |
| 8,350,032 B2 | 1/2013 | Neumann et al. |
| 8,916,356 B2 | 12/2014 | Hemker et al. |
| 2003/0087239 A1 | 5/2003 | Stanton et al. |
| 2004/0005582 A1* | 1/2004 | Shipwash ........ G01N 33/54366 435/6.19 |
| 2010/0196460 A1* | 8/2010 | Neumann ............ A61K 49/00 424/450 |
| 2012/0252127 A1 | 10/2012 | Gregor et al. |

OTHER PUBLICATIONS

McCallum et al, The Location of the Active Site of Blood Coagulation Factor VIIa above the Membrane Surface and Its Reorientation upon Association with Tissue Factor, The Journal of Biological Chemistry, 1996, vol. 271, No. 45, Issue of Nov. 8, pp. 28168-28175.*

* cited by examiner

*Primary Examiner* — Christine T Mui
(74) *Attorney, Agent, or Firm* — Lumen Patent Firm (57) ABSTRACT

Improved monitoring of one or more blood coagulation factors is provided. Factor-specific molecular probes having a dye-quencher arrangement are employed. In preferred embodiments, a compact integrated optical source and detector device is used for fluorescence measurements. Continuous and real-time monitoring of the activity of one or multiple blood factors is provided. Such real-time information can be used to automatically control delivery of drugs such as coagulants and/or blood thinners.

19 Claims, 9 Drawing Sheets

METHODS AND APPARATUS FOR RAPID MONITORING OF HEMOSTATIC STATE

CROSS REFERENCE TO RELATED APPLICATIONS

This application claims the benefit of U.S. provisional patent application 62/017,571, filed on Jun. 26, 2014, and hereby incorporated by reference in its entirety.

FIELD OF THE INVENTION

This invention relates to monitoring of hemostatic state.

BACKGROUND

The ability to monitor blood coagulation processes is important for effective hemostasis management, especially during surgeries and therapies such as hemodialysis.

Existing techniques that measure clotting time or assess the viscoelastic properties of blood often rely on highly trained personnel, use bulky and costly instruments, and only provide snapshots of the patient's blood condition at a specific time.

Schemes currently exist to monitor the concentration or activity of coagulation factors in blood via electrochemical, bioluminescence, and fluorescence techniques. These conventional approaches are often based on bulk-optics imaging systems that are very large and costly, and typically require at least 30 minutes for sample preparation and processing.

Examples include the following references. In US 2012/0252127, time-resolved coagulation and clotting properties are measured by imaging forward-scattered light. In U.S. Pat. No. 8,350,032, photoactive compounds designed to bind and inhibit serine proteases are considered. In U.S. Pat. No. 8,293,493, a method is provided for inferring generation of thrombin as a function of time calculated from fluorescence as a function of time.

SUMMARY

The present invention is directed to providing real-time, cost-effective medical diagnostics. In a preferred embodiment, we provide an extremely compact, cost-effective integrated semiconductor-based optical sensor platform with continuous monitoring capabilities. The platform includes monolithically integrated Vertical Cavity Surface Emitting Lasers (VCSELs) grown directly with sensitive photodetectors to enable miniaturized devices. These source and detector modules can be integrated with a microfluidic chip that delivers activatable fluorescent molecular probes and other liquids such as therapeutic doses of coagulants or blood thinners. A series of valves can allow for one-way sampling with the sensor placed in the line of existing extra-corporeal circuits. The entire platform can be operated wirelessly for automated sample analysis. The molecular probes demonstrate signal enhancement compared to controls in human plasma, with specificity, sensitivity, and time resolution that enables rapid diagnostics for early detection of thrombotic events and improved patient care.

In one embodiment of the present invention, extremely compact integrated semiconductor-based lasers and photodetectors provide real-time, continuous readout of light intensity from a biological sample that has been exposed to activatable fluorescent molecular probes. The integrated sensing platform monitors components of blood in extra-corporeal circuits, in vivo, or in vitro. The resulting measurements can provide continuous feedback on a patient's coagulation status, monitoring the efficacy of adjustments to the hemostatic system and enabling timely interventions.

Significant aspects of this work include providing real-time, continuously-measured coagulation data from activatable probes—in sharp contrast to conventional approaches where existing measurement capabilities only provide a snapshot of data at a fixed time, with a measurement process that can take 45 minutes or more. Typical blood testing in coagulation laboratories currently includes the drawing or aspiration of blood, sample preparation and centrifugation, data collection (often from a bulky piece of equipment that does not provide molecular information), analysis of results, and communication of the test results back to the patient's bedside. The ability to circumvent time-consuming and error-prone sample handling and transportation with a sensor that is integrated "in-line" offers substantial enhancements in a medical professional's ability to respond as events occur. Furthermore, the actual activity of particular coagulation factors is measured in this work, as opposed to existing methods that only extrapolate concentration or provide signs of coagulation without molecular specificity. This enables an unprecedented level of detailed and pertinent information to help provide more informed patient care.

BRIEF DESCRIPTION OF THE DRAWINGS

FIGS. 4-C show experimental results relating to principles of the invention.

DETAILED DESCRIPTION

Figure 1:
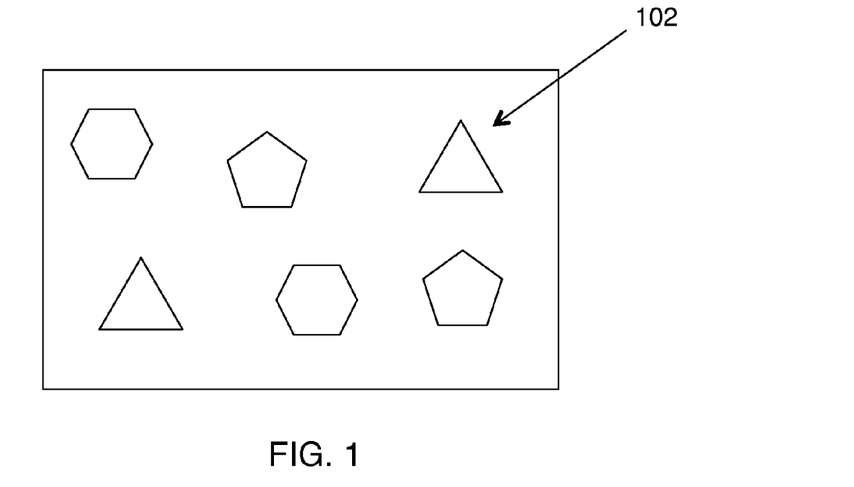
FIG. 1 schematically shows a blood sample having several distinct coagulation factors.

FIG. 1 schematically shows a blood sample having several distinct coagulation factors. In this example, several blood coagulation factors 102 (e.g., prothrombin, thrombin, tissue factor, fibrinogen, and factors VIIa, IXa, Xa, Va, VIIIa, and XIa) are schematically distinguished by being shown with different shapes.

Figure 2A:
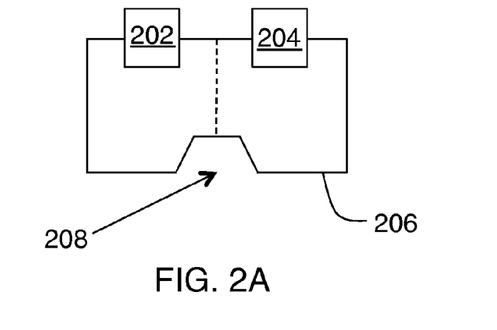
FIGS. 2A-C show operation of a molecular probe suitable for use in embodiments of the invention.
Figure 2B:
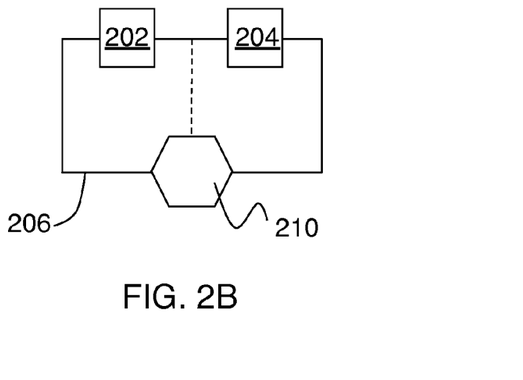
Figure 2C:
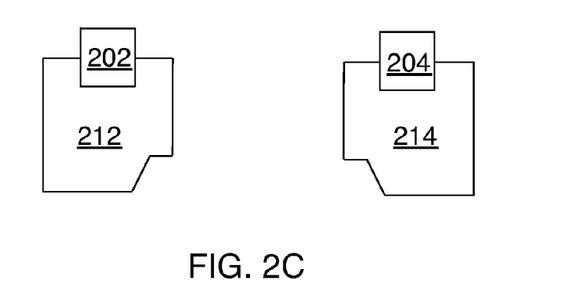

FIGS. 2A-C schematically show operation of a molecular probe suitable for use in embodiments of the invention. Here molecular probe species 206 includes a fluorescent dye 202 in proximity to a quencher 204 such that fluorescence from dye 202 is inhibited. Species 206 is specifically responsive (e.g., cleavage site 208) to a specific blood coagulation factor (e.g., blood factor 210) by cleaving to separate the fluorescent dye from the quencher (along the dotted line shown on FIGS. 2A-B). Molecular specificity is schematically shown here by the match between blood coagulation factor shape and the shape of cleavage site 208. Cleavage site 208 can be a specific peptide sequence that is designed to be cleaved by the target blood coagulation factor. The chemistry and physical configuration of the probe, including the peptide sequence, dye, quencher, and any desired spacers, can be optimized to elicit maximum fluorescence signal upon cleaving, with detection of the cleaving activity from a designed optical source and an optical detector. For example, when the target blood coagulation factor is active in the vicinity of probe species 206, it can cleave the peptide sequence, thereby separating the dye and quencher such that the measured fluorescence changes. The resulting cleaved configuration is shown on FIG. 2C, where fragments 212 and 214 are formed. Because dye 202 on fragment 212 is no longer in fixed proximity to quencher 204, its fluorescence is no longer inhibited. The probe (peptide sequence, dye, quencher, and any spacers) spectral characteristics can be designed to match the wavelength range of the optical unit that measures the fluorescence over time.

Because of the molecular specificity of probe species 206, it is possible to simultaneously measure two or more different blood coagulation factors all in real-time. In these embodiments, a different probe species 206 is used for each blood coagulation factor of interest. For example, one probe species could match the blood coagulation factor corresponding to hexagonal symbols on FIG. 1, and another probe species could match the blood coagulation factor corresponding to triangular symbols on FIG. 1. An exemplary measurement showing blood coagulation factor specificity is described below in connection with FIG. 4C.

The dyes 202 used on the different probe species can either be the same or distinct. If the same dye is used for each probe species, then the fluorescence signals for each blood coagulation factor can be obtained by measuring the blood sample in several fluidic channels simultaneously. Here a different probe species is provided to each of the fluidic channels, and each fluidic channel has its corresponding optical source and detector.

If different dyes that fluoresce at different wavelengths are used for each probe species, then the fluorescence signals for each blood coagulation factor can be obtained by measuring the blood sample in a single fluidic channel. Here signals from the different probe species can be spectroscopically distinguished, and all probe species are simultaneously provided to the single fluidic channel. A single optical source and detector can be used in this configuration, provided that the single source can cause all relevant dyes to fluoresce. Multiple sources at different wavelengths can be employed if that is needed to cause all relevant dyes to fluoresce. Suitable wavelengths include but are not limited to visible and near-infrared ranges, as shown on FIGS. 4A-C.

Figure 2D:
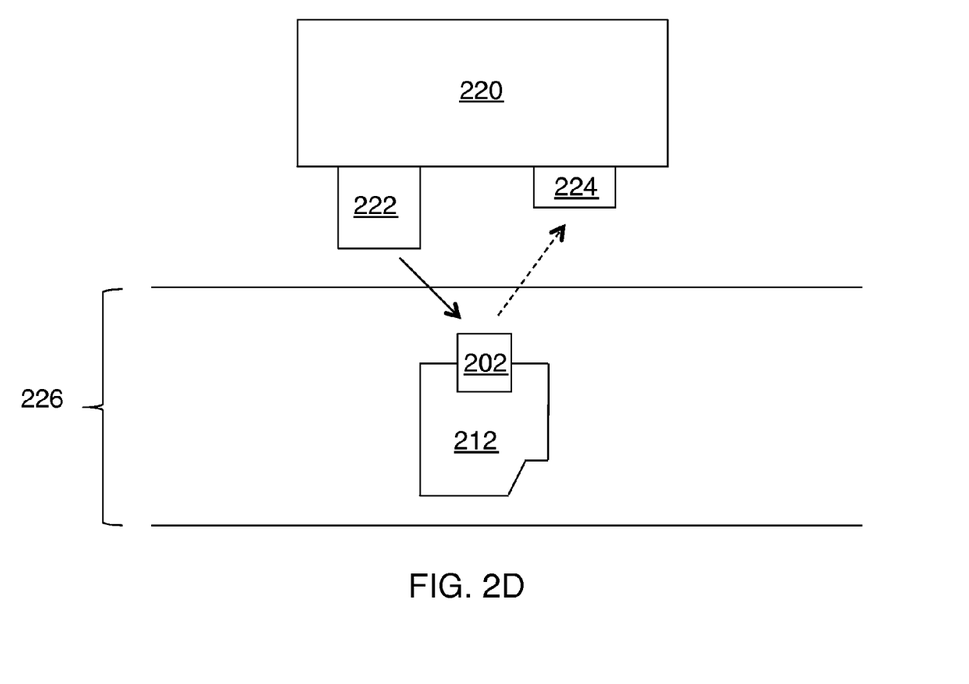
FIG. 2D shows detection of a cleaved part of the molecular probe via fluorescence.

FIG. 2D shows detection of a cleaved part of the molecular probe species 206 via fluorescence. This example shows a preferred embodiment where an optical source 222 illuminates dye 202 on fragment 212 to generate fluorescence that is received by detector 224. Here fragment 212 is contained within a fluidic channel 226. Preferably optical source 222 and detector 224 are monolithically integrated onto a single substrate 220, thereby forming an integrated circuit. More preferably, optical source 222 is a vertical cavity surface emitting laser (VCSEL), to minimize the size of the device and to leverage semiconductor fabrication processing techniques for low-cost manufacturing and testing. Preferably fluidic channel 226 is part of a microfluidic system configured to provide blood samples for fluorescence measurements.

This approach of integrating VCSELs and photodetectors can provide an extremely compact, cost-effective, arrayable optical sensing platform. In a preferred embodiment, the VCSEL/detector chip is placed directly adjacent to (and/or integrated with) a microfluidic chip that holds the blood sample. As indicated below, the microfluidic chip can be positioned in the line of an extra-corporeal circuit.

Thus a first exemplary embodiment of the invention is a method for monitoring hemostatic state with molecular specificity. This method includes the following steps.

1) Providing a blood sample.

2) Providing a first molecular probe species (e.g., 206 on FIGS. 2A-C) to the blood sample. The first molecular probe species has a first fluorescent dye in proximity to a first quencher. The first molecular probe species is responsive to a first blood coagulation factor (e.g., 210 on FIG. 2B) by cleaving to separate the first fluorescent dye from the quencher (e.g., as shown on FIG. 2C).

3) Optically measuring the activity of the first blood coagulation factor by illuminating the blood sample with an optical source and measuring fluorescent radiation from the first fluorescent dye (e.g., with an optical detector as shown on FIG. 2D).

The above-described method relates to detection of a single blood coagulation factor. This approach can be extended to detection of multiple blood coagulation factors as follows.

4) Providing one or more second molecular probe species to the blood sample. Each second molecular probe species has a corresponding second fluorescent dye in proximity to a quencher. Each second molecular probe species is responsive to a corresponding second blood coagulation factor by cleaving to separate the second fluorescent dye from the quencher. Here the first fluorescent dye and the second fluorescent dye(s) can either be all the same, or all distinct. Furthermore, it is also possible for the first and second fluorescent dyes to have any intermediate configuration between all being the same and all being distinct.

5) Optically measuring the activity of the one or more second blood coagulation factors by illuminating the blood sample with the optical source and measuring fluorescent radiation from the one or more second fluorescent dyes. As indicated above, all measurements can be done with a single detector, or one detector can be employed for each coagulation factor being monitored.

This approach allows for the continuous and real-time monitoring of the activity of the first blood coagulation factor (in the case where only a single blood coagulation factor is monitored). If multiple blood coagulation factors are monitored continuously and in real-time, this amounts to continuous real-time monitoring of the activity of the first blood coagulation factor and of the activity of the one or more second blood coagulation factors.

Figure 3:
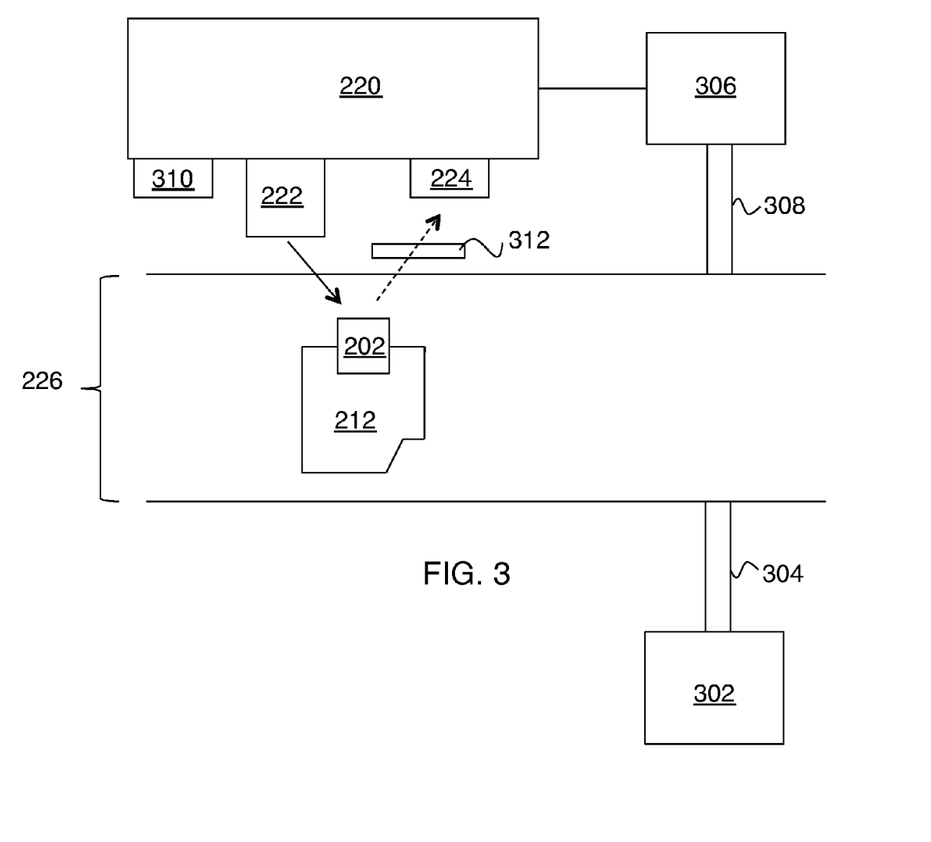
FIG. 3 shows some optional modifications of the configuration of FIG. 2D.

FIG. 3 shows further details and some optional modifications of the configuration of FIG. 2D. It is convenient to describe the blood sample handling apparatus in terms of two units. The first unit provides the blood sample (e.g., fluidic channel 226). The second unit provides the molecular probe species to the blood sample. Here this is schematically shown by reservoir 302 connected to channel 226 via channel 304.

A further function that can optionally be provided by the system of FIG. 3 is delivery from reservoir 306 of therapeutic doses of medications such as coagulants or blood thinners in response to measured activity of blood coagulation factors. Such medication delivery can be by way of channel 308 in a configuration where blood flow in fluidic channel 226 returns to the patient's body (as in FIG. 6 below). Another optional feature shown on FIG. 3 is wireless subsystem 310 for reporting measured activity of the blood coagulation factor(s).

In some embodiments, an optical filter 312 (which may be tunable) is included in the light path of one or multiple detectors to allow for reference measurements or differentiation of emitted fluorescence signals. Although FIG. 3 shows filter 312 as an off-chip component disposed between the blood sample and the detector, other locations for the filter are possible, especially in cases where the VCSEL, detector and filter are all monolithically integrated. For example, in cases where the VCSEL is above the detector in a vertical layer stack, the filter can be disposed between the VCSEL and the detector.

A second exemplary embodiment of the invention is an apparatus for monitoring hemostatic state with molecular specificity. This apparatus includes the following components.

1) A first unit (e.g., fluid channel 226 on FIG. 3) configured to provide a blood sample.

2) A second unit (e.g., 302 and 304 on FIG. 3) configured to provide a first molecular probe species to the blood sample. The first molecular probe species has a fluorescent dye in proximity to a first quencher. The first molecular probe species is responsive to a first blood coagulation factor by cleaving to separate the fluorescent dye from the quencher.

3) An optical unit comprising an optical source (e.g., 222 on FIG. 3, which may have a tunable emission wavelength) and an optical detector (e.g., 224 on FIG. 3). The optical detector is configured to measure activity of the first blood coagulation factor by measuring fluorescent radiation from the first fluorescent dye responsive to illumination from the optical source.

This apparatus can be modified to simultaneously measure activity of two or more coagulation factors. Thus the optical unit can include two or more optical detectors and/or two or more optical sources as needed. Some embodiments may also make use of tunable optical filters and/or tunable optical sources.

Preferably the first unit and the second unit are configured as a microfluidic system in optical communication with the integrated circuit.

Figure 4A:
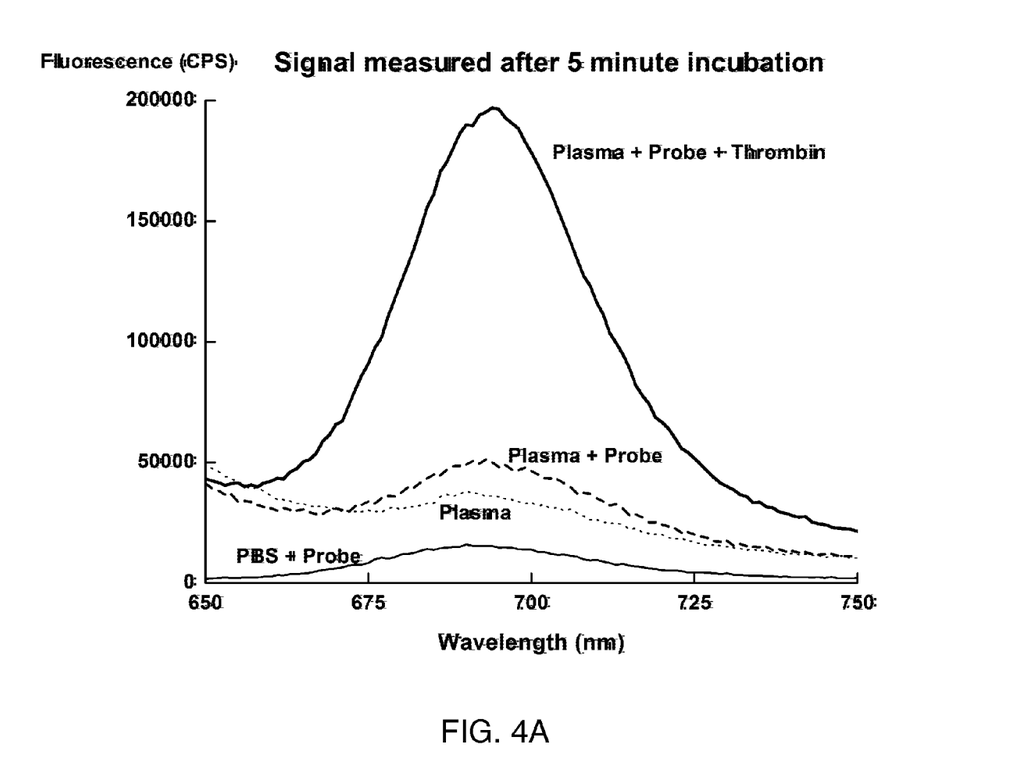
Figure 4B:
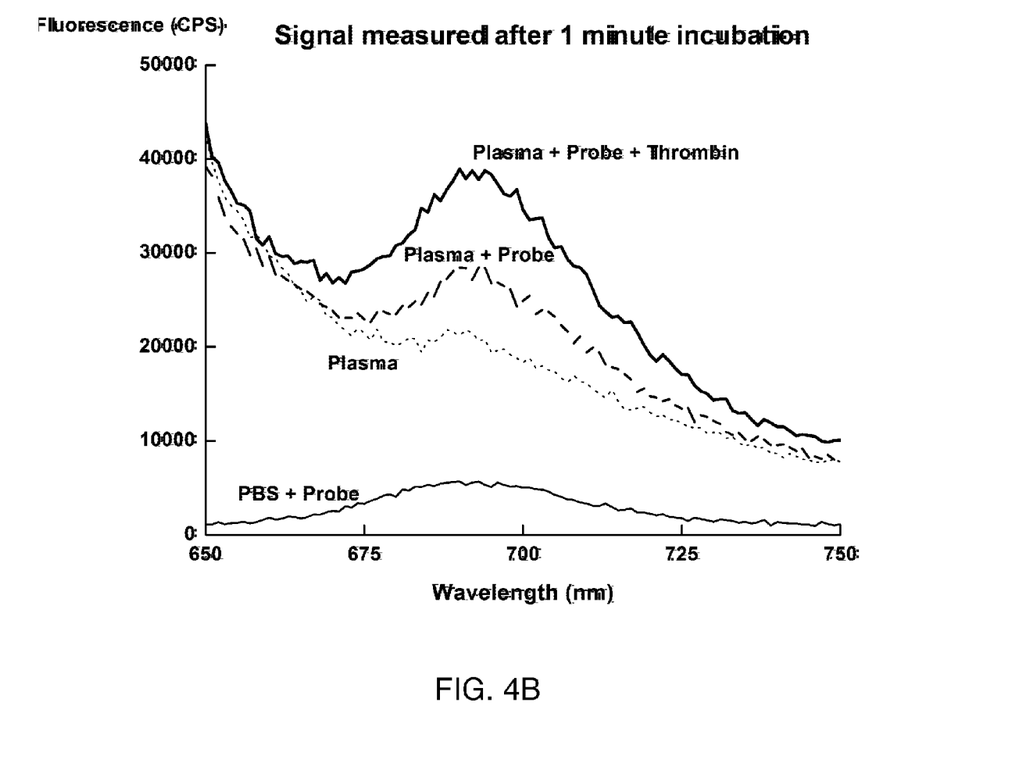
Figure 4C:
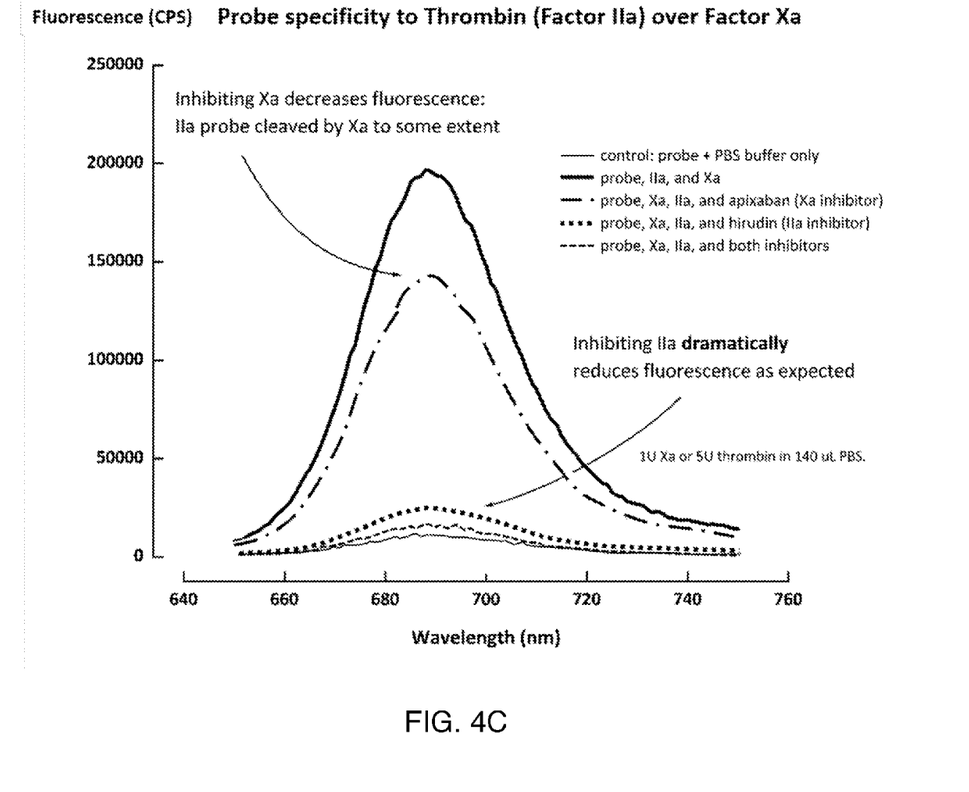

FIGS. 4A-C show experimental results relating to principles of the invention. Using a benchtop spectrophotometer, four samples were monitored for fluorescence after both 5 minutes (FIG. 4A) and 1 minute (FIG. 4B). The human plasma sample, as well as the sample having the probe surrounded in phosphate buffered saline (PBS), both showed low fluorescence as expected. The sample with the probe surrounded in plasma showed a marginal background fluorescence, in contrast to the sample having the probe combined with activated thrombin in plasma. Measurable contrast showing activity in the desired wavelength range is shown for both 5 minute incubations as well as 1 minute measuring time after the solutions were created. Moreover, FIG. 4C demonstrates the designed behavior and specificity of the probe in solutions of thrombin (also known as Factor IIa), Factor Xa, and their respective inhibitors. When the thrombin inhibitor is added, thrombin no longer cleaves the probe; in contrast, the Factor Xa and Factor Xa inhibitors do not strongly affect the fluorescence measured, as expected.

Practice of the invention does not depend critically on how the blood sample is obtained. Several possibilities are shown on FIGS. 5-8.

Figure 5:
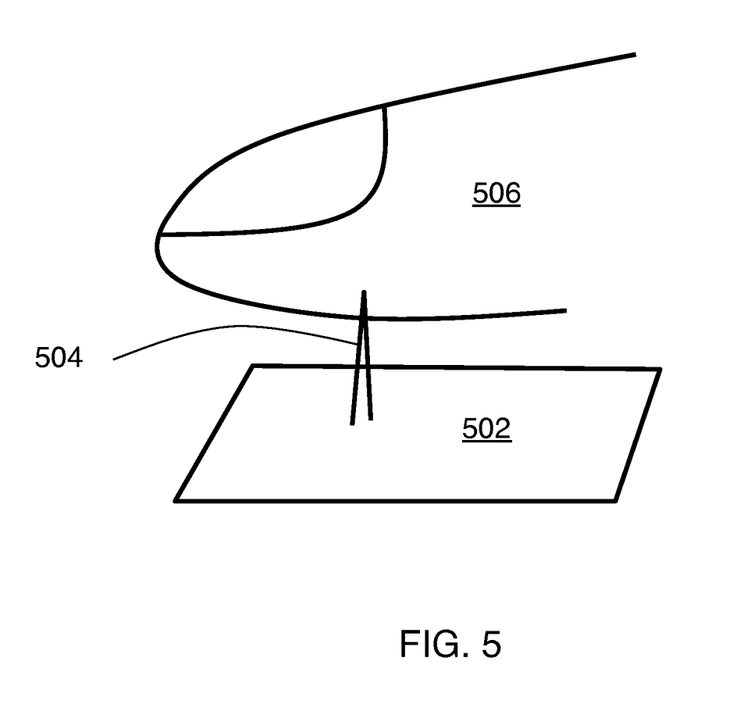
FIG. 5 schematically shows obtaining a blood sample with a needle.

FIG. 5 schematically shows obtaining a blood sample with a needle. Here a needle 504 is in fluid communication with coagulation factor monitoring system 502 that operates according to the above described principles. For example, a suitable blood sample can be obtained by a blood draw from a finger 506 of a patient. This amounts to extracting the blood sample from a patient for in vitro measurement. Simple needle pricks can be used to provide the small amounts of blood needed. With a sterilizable interface and multiple channels, this embodiment could allow for rapid comparison of different patients on a single analysis platform.

Figure 6:
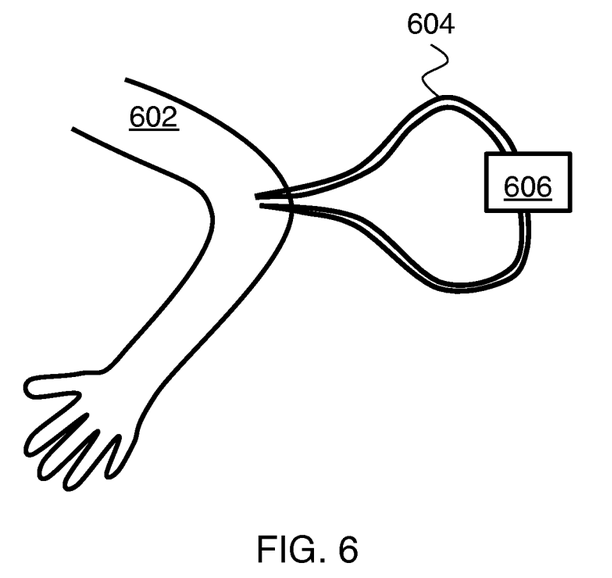
FIG. 6 schematically shows continuous blood monitoring in an extra-corporeal loop.

FIG. 6 schematically shows continuous blood monitoring in an extra-corporeal loop. This is an important preferred embodiment, where coagulation factor monitoring system 606 that operates according to the above described principles is inserted in-line in an extra-corporeal loop 604 that circulates blood from patient 602. This amounts to continuous, real-time monitoring of blood in an extra-corporeal circuit. This is the preferred embodiment for applications such as automatic delivery of drugs (e.g., coagulants and/or blood thinners) to a patient in response to measured changes in hemostatic state.

Figure 7:
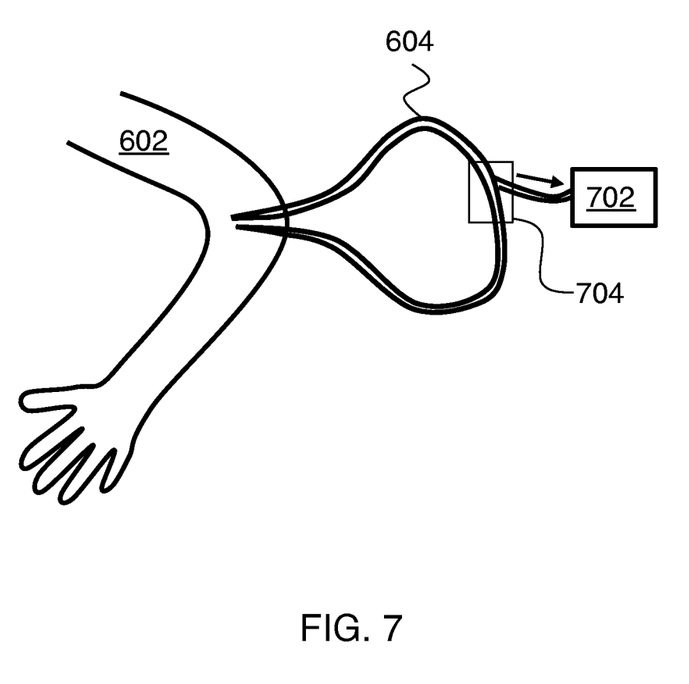
FIG. 7 schematically shows blood monitoring by sampling from an extra-corporeal loop.

FIG. 7 schematically shows blood monitoring by sampling from an extra-corporeal loop. In this example, coagulation factor monitoring system 702 that operates according to the above described principles is connected to extra-corporeal loop 604 by a one-way valve 704. This allows for "in-line" one-way sampling using existing extra-corporeal circuits. In this embodiment, the coagulation factor monitoring system 702 need not be integrated "in the line" of an extra-corporeal circuit for rapid, continuous monitoring.

Figure 8:
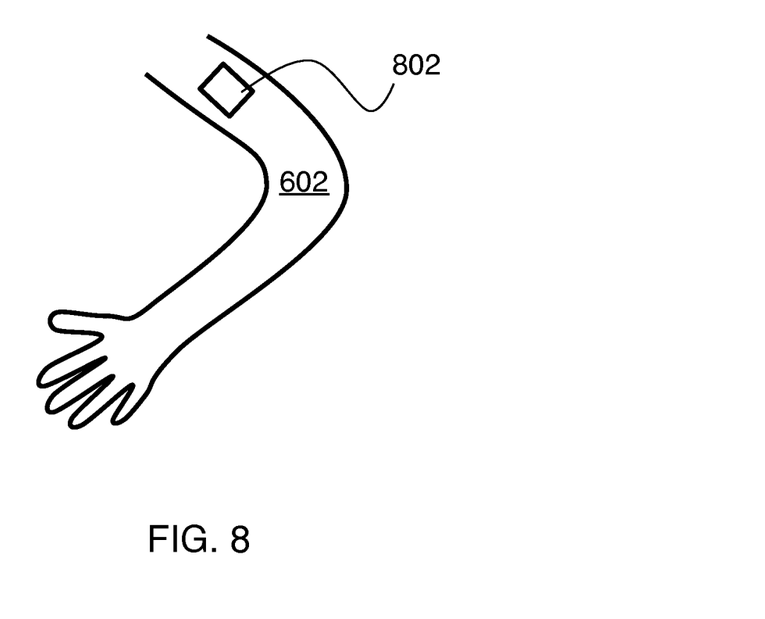
FIG. 8 schematically shows blood monitoring using a subcutaneous implant.

FIG. 8 schematically shows blood monitoring using a subcutaneous implant or a skin patch. In this example, an implant 802 or skin patch 802 is configured to provide blood coagulation factor activity measurements according to the above described principles. The molecular probes can be delivered to the patient either systemically or in proximity to implant 802. This amounts to in vivo, use for a single patient. One could periodically inject a specific fluorescent molecular probe into the patient's blood stream, and monitor the optical signal by utilizing a laser/detector module that is pressed against the patient's skin (i.e., skin patch) or implanted subcutaneously.

The invention claimed is:

1. A method for monitoring hemostatic state with molecular specificity, the method comprising:
   providing a blood sample;
   providing a first molecular probe species to the blood sample, wherein the first molecular probe species has a first fluorescent dye in proximity to a first quencher, and wherein the first molecular probe species is responsive to a first blood coagulation factor by cleaving to separate the first fluorescent dye from the first quencher;
   optically measuring the activity of the first blood coagulation factor by illuminating the blood sample with first optical radiation and measuring first fluorescent radiation from the first fluorescent dye.

2. The method of claim 1, further comprising:
   providing one or more second molecular probe species to the blood sample, wherein each second molecular probe species has a second fluorescent dye in proximity to a second quencher, and wherein each second molecular probe species is responsive to a corresponding second blood coagulation factor by cleaving to separate the second fluorescent dye from the second quencher;
   optically measuring the activity of the one or more second blood coagulation factors by illuminating the blood sample with second optical radiation and measuring second fluorescent radiation from the one or more second fluorescent dyes.

3. The method of claim 2, wherein the activity of the first blood coagulation factor and the activity of the one or more second blood coagulation factors are monitored continuously and in real-time.

4. The method of claim 2, further comprising adjusting a medication dose in response to measurement of activity of the first blood coagulation factor and measurement of activity of the one or more second blood coagulation factors.

5. The method of claim 1, wherein the providing a blood sample comprises continuous, real-time monitoring of blood in an extra-corporeal circuit.

6. The method of claim 1, wherein the providing a blood sample comprises sampling blood from an extra-corporeal circuit using a one-way valve.

7. The method of claim 1, wherein the providing a blood sample comprises disposing a sensor in vivo such that the sensor is responsive to fluorescence from blood.

8. The method of claim 7, wherein the sensor is disposed subcutaneously such that fluorescent radiation from the blood sample can be measured with the sensor non-invasively.

9. The method of claim 1, wherein the providing a blood sample comprises extracting the blood sample from a patient for in vitro measurement.

10. The method of claim 1, wherein the activity of the first blood coagulation factor is monitored continuously and in real-time.

11. The method of claim 1, further comprising adjusting a medication dose in response to measurement of activity of the first blood coagulation factor.

12. Apparatus for monitoring hemostatic state with molecular specificity, the apparatus comprising:
a first unit configured to provide a blood sample;
a second unit configured to provide a first molecular probe species to the blood sample, wherein the first molecular probe species has a fluorescent dye in proximity to a first quencher, and wherein the first molecular probe species is responsive to a first blood coagulation factor by cleaving into separate fragments to separate the fluorescent dye from the quencher, wherein the fluorescent dye is on one of the fragments and the quencher is on another of the fragments; and
an optical unit comprising an optical source and an optical detector, wherein the optical detector is configured to measure activity of the first blood coagulation factor by measuring fluorescent radiation from the first fluorescent dye responsive to illumination from the optical source.

13. The apparatus of claim 12, wherein the optical source comprises a vertical cavity surface emitting laser (VCSEL).

14. The apparatus of claim 13 wherein the VCSEL and the optical detector are monolithically integrated such that the optical unit is a single integrated circuit.

15. The apparatus of claim 14, wherein the first unit and the second unit are configured as a microfluidic system in optical communication with the integrated circuit.

16. The apparatus of claim 12, further comprising a drug delivery subsystem configured to automatically alter doses of one or more medications in response to measurement of the activity of the first blood coagulation factor.

17. The apparatus of claim 12, further comprising a wireless communication subsystem for reporting measured activity of the first blood coagulation factor.

18. The apparatus of claim 12, wherein the optical source has a tunable emission wavelength.

19. The apparatus of claim 12, further comprising a tunable optical filter disposed between the blood sample and the optical detector.

* * * * *